United States Patent
Suzuki

(10) Patent No.: US 8,841,485 B2
(45) Date of Patent: Sep. 23, 2014

(54) LIQUID PHENOL RESIN AND METHOD OF PREPARING THE SAME

(75) Inventor: Yuji Suzuki, Fujieda (JP)

(73) Assignee: Sumitomo Bakelite Co., Ltd., Tokyo (JP)

( * ) Notice: Subject to any disclaimer, the term of this patent is extended or adjusted under 35 U.S.C. 154(b) by 0 days.

(21) Appl. No.: 13/812,063

(22) PCT Filed: Jul. 22, 2011

(86) PCT No.: PCT/JP2011/066712
§ 371 (c)(1),
(2), (4) Date: Jan. 24, 2013

(87) PCT Pub. No.: WO2012/014807
PCT Pub. Date: Feb. 2, 2012

(65) Prior Publication Data
US 2013/0123538 A1 May 16, 2013

(30) Foreign Application Priority Data

Jul. 27, 2010 (JP) ................................. 2010-167934

(51) Int. Cl.
*C07C 211/00* (2006.01)
*C07C 69/00* (2006.01)
*C07C 213/02* (2006.01)
*C07C 215/48* (2006.01)
*C08G 73/02* (2006.01)

(52) U.S. Cl.
CPC ............. *C07C 215/48* (2013.01); *C07C 213/02* (2013.01); *C08G 73/02* (2013.01)
USPC ............................. 564/336; 564/461; 560/130

(58) Field of Classification Search
None
See application file for complete search history.

(56) References Cited

U.S. PATENT DOCUMENTS

2009/0259003 A1  10/2009  Walker et al.

FOREIGN PATENT DOCUMENTS

| CA | 1076289 A | 4/1980 |
| JP | 52-070000 A | 6/1977 |
| JP | 61-171717 A | 8/1986 |
| JP | 08-143752 A | 6/1996 |
| JP | 09-059599 A | 3/1997 |
| JP | 2000-044642 A | 2/2000 |
| JP | 2007-002032 A | 1/2007 |
| JP | 2009-067921 A | 4/2009 |
| JP | 2009-249633 A | 10/2009 |

OTHER PUBLICATIONS

JP-2009067921 machine translation, 2009, 6 pages.*
International Search Report of PCT/JP2011/066712, mailing date of Oct. 25, 2011.

* cited by examiner

*Primary Examiner* — Clinton Brooks
(74) *Attorney, Agent, or Firm* — Westerman, Hattori, Daniels & Adrian, LLP

(57) ABSTRACT

According to the present invention, a liquid phenol resin that has excellent characteristics of a phenol resin, such as thermal resistance and hardenability, and can produce a molded product having excellent flexibility, and a method of preparing the resin are provided.

The present invention relates to a liquid phenol resin obtained by reacting (A) oils and (B) phenols with (C) a secondary and/or a tertiary alkylamine compound, wherein a nitrogen content based on the whole liquid phenol resin is 3% by weight to 30% by weight, and (A):(B)=10:90 to 90:10.

5 Claims, No Drawings

LIQUID PHENOL RESIN AND METHOD OF PREPARING THE SAME

TECHNICAL FIELD

The present invention relates to a liquid phenol resin and a method of preparing the same.

Priority is claimed on Japanese Patent Application No. 2010-167934, filed Jul. 27, 2010, the content of which is incorporated herein by reference.

BACKGROUND ART

A phenol resin as a thermosetting resin is widely used mainly as a binder for binding materials that become a substrate of a molded product to each other. Having excellent mechanical characteristics, electrical characteristics, and adhesiveness, the phenol resin is used in various fields.

The phenol resin is used for impregnation. Examples of uses in impregnation include a wet friction material, a prepreg, a laminate, a C-C composite, Fiber Reinforced Plastic (FRP), a coated abrasive, and the like. For use in impregnation, a resol type liquid phenol resin is generally used. Further improvement is increasingly required for the characteristics of the phenol resin for use in impregnation, and particularly, for the purpose of improving toughness, the improvement of the flexibility of the phenol resin has been required increasingly. However, though having excellent mechanical characteristics, a hardened material of the general phenol resin has a property of being hard and brittle, so the resin is not necessarily excellent in flexibility.

Therefore, as a method of solving the above problem, an attempt at improving flexibility by using drying oil or the like as a modifier in a reaction for synthesizing the phenol resin has been examined (for example, see PTL 1).

However, such a modified phenol resin shows a marked decrease in strength after heat history, and has a problem of a short cycle life.

CITATION LIST

Patent Literature

[PTL 1] Japanese Unexamined Patent Application, First Publication No. H09-59599

SUMMARY OF INVENTION

Technical Problem

The present invention provides a liquid phenol resin that has excellent characteristics of a phenol resin, such as thermal resistance and hardenability, and can produce an excellent molded product in which the improvement of toughness resulting from the improvement of flexibility is compatible with the strength after heat history, and provides a method of preparing the resin.

Solution to Problem

The above objects are achieved by the following aspects [1] to [8] of the present invention.

[1] A liquid phenol resin obtained by reacting (A) oils and (B) phenols with (C) a secondary and/or a tertiary alkylamine compound.

[2] The liquid phenol resin according to aspect [1], wherein the (A) oils include at least one or more kinds selected from the group consisting of cashew oil, linseed oil, tung oil, castor oil, and tall oil.

[3] The liquid phenol resin according to aspect [1] or [2], wherein a nitrogen content based on the whole liquid phenol resin is 3% by weight to 30% by weight.

[4] The liquid phenol resin according to aspects [1] to [3], wherein a weight ratio between the (A) oils and the (B) phenols is (A):(B)=10:90 to 90:10.

[5] The liquid phenol resin according to any one of aspects [1] to [4], wherein the (C) secondary and/or tertiary alkylamine compound includes hexamethylenetetramine.

[6] The liquid phenol resin according to any one of aspects [1] to [5], which is obtained by reacting the (A) oils and the (B) phenols with the (C) secondary and/or tertiary alkylamine compound, in a molar ratio of (C)/{(A)+(B)}=0.13 to 0.35.

[7] The liquid phenol resin according to any one of aspects [1] to [6], which is used for impregnation.

[8] A method of preparing a liquid phenol resin which is the liquid phenol resin according to any one of aspects [1] to [7], including reacting (A) oils and (B) phenols with (C) a secondary and/or a tertiary alkylamine compound without performing a step of dehydration.

Advantageous Effects of Invention

If the liquid phenol resin of the present invention is used as a binder, a molded product having excellent thermal resistance, hardenability, and flexibility can be obtained.

DESCRIPTION OF EMBODIMENTS

Hereinafter, the liquid phenol resin of the present invention and the method of preparing the resin will be described in detail.

The liquid phenol resin of the present invention is obtained by reacting (A) oils and (B) phenols with (C) a secondary and/or a tertiary alkylamine compound.

In addition, the method of preparing a liquid phenol resin of the present invention includes reacting (A) oils and (B) phenols with (C) a secondary and/or a tertiary alkylamine compound without performing a step of dehydration.

First, the liquid phenol resin of the present invention will be described in detail.

(A) Oils

The oils used for the liquid phenol resin of the present invention include cashew oil, linseed oil, tung oil, castor oil, tall oil, and the like. Particularly, cashew oil is an oily liquid collected from the shells of cashew nuts, and contains cardanol and cardol, which are phenol derivatives, as main components. These can be used alone, or two or more kinds thereof can be used concurrently.

If the oils are used for the liquid phenol resin of the present invention, it is possible to impart flexibility to the obtained liquid phenol resin.

(B) Phenols

Examples of phenols used for the liquid phenol resin of the present invention include cresols such as phenol, o-cresol, m-cresol, and p-cresol, xylenols such as 2,3-xylenol, 2,4-xylenol, 2,5-xylenol, 2,6-xylenol, 3,4-xylenol, and 3,5-xylenol, ethylphenols such as o-ethylphenol, m-ethylphenol, and p-ethylphenol, butylphenols such as isopropylphenol, butylphenol, and p-tert-butylphenol, alkylphenols such as p-tert-amylphenol, p-octylphenol, p-nonylphenol, and p-cumylphenol, halogenated phenols such as fluorophenol, chlorophenol, bromophenol, and iodophenol, substituted monovalent phenols such as p-phenylphenol, aminophenol, nitrophenol, dinitrophenol, and trinitrophenol, monovalent phenols such as 1-naphthol and 2-naphthol, polyvalent phenols such as resorcin, alkylresorcins, pyrogallol, catechol, alkylcatechols, hydroquinone, alkylhydroquinones, phloroglucine, bisphenol A, bisphenol F, bisphenol S, dihydroxynaphthalene, and the like. These can be used alone, or two or more kinds thereof can be used as a mixture.

Among these phenols, those selected from phenol, cresols, and bisphenol A are preferable. If such phenols are used, it is possible to improve the mechanical strength in a molded product using the liquid phenol resin of the present invention.

(C) Secondary and/or Tertiary Alkylamine Compound

Examples of the secondary and/or tertiary alkylamine compound used for the liquid phenol resin of the present invention include dimethylamine and diethylamine as the secondary alkylamine compound, and triethylamine, tetramethylethylenediamine, and hexamethylenetetramine as the tertiary alkylamine compound, and the like. These can be used alone, or two or more kinds thereof can be used concurrently.

Among these, hexamethylenetetramine is preferably used. If this compound is used, it is possible to decrease the cost even if a nitrogen content is increased.

In the liquid phenol resin of the present invention, a weight ratio between the (A) oils and the (B) phenols is preferably (A):(B)=10:90 to 90:10, and more preferably 25:75 to 75:25. In this ratio, it is possible to make the flexibility of the obtained liquid phenol resin to be compatible with a heat-resistant strength.

In the liquid phenol resin of the present invention, a molar number of the (C) secondary and/or tertiary alkylamine compound based on 1 mol as a total molar number of the (A) oils and the (B) phenols is preferably 0.13 mol to 0.35 mol, and more preferably 0.15 mol to 0.30 mol.

In such a molar number, it is possible to improve the flexibility of a molded product while maintaining excellent impregnating properties, when the liquid phenol resin of the present invention is used for impregnation.

In the liquid phenol resin of the present invention, a nitrogen content based on the whole liquid phenol resin is preferably 3% by weight to 30% by weight, and more preferably 5% by weight to 10% by weight.

If the nitrogen content is larger than this, viscosity increases, which makes it difficult to remove from a containing vessel. Moreover, if the nitrogen amount is smaller than the above value, the effect of improving thermal resistance is diminished.

The liquid phenol resin of the present invention is obtained by reacting the above-described (A) oils and (B) phenols with the (C) secondary and/or tertiary alkylamine compound.

The liquid phenol resin of the present invention can be obtained even if a catalyst is not used, but if necessary, an alkaline catalyst can be used. As the alkaline catalyst, alkaline substances include hydroxides of alkali metals, such as sodium hydroxide, lithium hydroxide, and potassium hydroxide, aqueous ammonia, tertiary amines such as triethylamine, oxides and hydroxides of alkaline earth metals such as calcium, magnesium, and barium, and sodium carbonate can be used alone, or two or more kinds of these can be used concurrently.

Though not particularly limited, the amount of the alkaline catalyst used can be generally set to 0.01 mol to 0.1 mol based on 1 mol as a total molar number of the (A) oils and the (B) phenols.

In the liquid phenol resin of the present invention, an organic solvent can be used to dilute the resin. As the organic solvent used for dilution, for example, alcohol-based organic solvents such as methanol, ethanol, isopropanol, and butanol, ketone-based organic solvents such as acetone, methyl ethyl ketone, and methyl isobutyl ketone, aromatic hydrocarbon solvents such as toluene and ethylbenzene, and a mixture of these can be used, though the organic solvents are not limited to these.

Next, the method of preparing a liquid phenol resin of the present invention will be described.

The method of preparing a liquid phenol resin of the present invention includes reacting (A) oils and (B) phenols with (C) a secondary and/or a tertiary alkylamine compound without performing a step of dehydration.

Specifically, since the reaction is performed without using a water-containing raw material such as an aqueous formalin solution, a step of dehydration is unnecessary.

In this manner, it is possible to obtain a liquid phenol resin with an excellent yield, without discharging waste liquid that is produced in the step of dehydration. In addition, since water is not contained, drying can be rapidly performed when preparing an impregnation material.

The liquid phenol resin of the present invention can be particularly suitably used for impregnation. Examples of use in impregnation include a wet friction material, a prepreg, a laminate, a C-C composite, Fiber Reinforced Plastic (FRP), a coated abrasive, and the like.

When the liquid phenol resin of the present invention is used as an impregnation material, a paper substrate containing metal fibers or carbon fibers and chemical fibers as main components may be impregnated with the liquid phenol resin of the present invention, and the resultant may be fired and hardened to obtain an impregnation material.

The obtained impregnation material has excellent characteristics of a phenol resin, such as thermal resistance and hardenability, and excellent flexibility.

EXAMPLES

Hereinafter, the present invention will be described in detail based on examples.

The term "part(s)" described herein refers to "part(s) by weight", and "%" refers to "% by weight".

1. Preparation of Liquid Phenol Resin

Example 1

1000 parts by weight of phenol, 1000 parts by weight of cashew oil, 50 parts by weight of methanol, 250 parts by weight of acetone, 500 parts by weight of hexamethylenetetramine, and 40 parts by weight of a 50% aqueous sodium hydroxide solution were put in a reactor provided with a stirring device, a reflux condenser, and a thermometer. The temperature of the reactor was increased to 95° C. by heating, and the temperature was maintained for 3 hours.

Thereafter, 1800 parts by weight of acetone was added thereto, and the reactor was cooled to a temperature equal to or lower than 40° C., thereby obtaining 4400 parts by weight of a liquid phenol resin.

Example 2

4300 parts by weight of a liquid phenol resin was obtained in the same manner as in Example 1, except that 350 parts by weight of hexamethylenetetramine was used.

Example 3

4700 parts by weight of a liquid phenol resin was obtained in the same manner as in Example 1, except that 670 parts by weight of hexamethylenetetramine was used.

Example 4

4400 parts by weight of a liquid phenol resin was obtained in the same manner as in Example 1, except that 1500 parts by weight of phenol and 500 parts by weight of cashew oil were used.

Example 5

4400 parts by weight of a liquid phenol resin was obtained in the same manner as in Example 1, except that 500 parts by weight of phenol and 1500 parts by weight of cashew oil were used.

Example 6

4400 parts by weight of a liquid phenol resin was obtained in the same manner as in Example 1, except that cashew oil was replaced with tung oil.

Comparative Example 1

In Example 1, reaction was performed using 1600 parts by weight of a 37% aqueous formalin solution instead of 500 parts by weight of hexamethylenetetramine. The resultant was dehydrated for 30 minutes at 80° C. under reduced pressure, and 1800 parts by weight of acetone was added thereto, followed by cooling to a temperature equal to or lower than 40° C., thereby obtaining 4100 parts by weight of a liquid phenol resin.

2. Evaluation of Liquid Phenol Resin

By using the liquid phenol resin obtained in the examples and the comparative example, impregnated paper was prepared. As a substrate, commercially available filter paper (120 mm×10 mm×1 mm) was used.

The liquid phenol resin obtained in the examples and the comparative example was diluted with methanol to prepare a solution with a resin concentration of 35%, and the above filter paper was impregnated with the solution. Thereafter, the paper was dried for 30 minutes in an oven at 190° C. and hardened, thereby obtaining test pieces. A yielded tensile strength and a tensile elastic modulus of the obtained test pieces were measured respectively in a natural state as well as after the test pieces were treated for an hour at 240° C., based on JIS P 8113 "Paper and board—Determination of tensile properties".

The results of the above evaluation are summarized in Table 1.

TABLE 1

| | Example 1 | Example 2 | Example 3 | Example 4 | Example 5 | Example 6 | Comparative Example 1 |
|---|---|---|---|---|---|---|---|
| Tensile strength (MPa) | 24.4 | 22.0 | 18.6 | 23.0 | 22.1 | 24.0 | 17.1 |
| Tensile elastic modulus (MPa) | 840 | 902 | 818 | 950 | 820 | 815 | 942 |
| Tensile strength after treatment at 240° C. (MPa) | 16.9 | 15.6 | 13.8 | 17.0 | 16.6 | 16.0 | 10.1 |
| Tensile elastic modulus after treatment at 240° C. (MPa) | 800 | 820 | 777 | 830 | 760 | 781 | 753 |

Examples 1 to 6 are the liquid phenol resin of the present invention. From the low elastic modulus, it was understood that the obtained hardened material of the resin has excellent flexibility, and from the fact that the strength was maintained to a high degree after the treatment at 240° C., it was understood that the hardened material has excellent thermal resistance.

On the other hand, Comparative Example 1 is a resol type resin obtained using cashew oil, phenol, and formaldehyde. In this resin, the tensile strength and tensile elastic modulus after the treatment at 240° C. were markedly decreased, and a resin having excellent thermal resistance could not be obtained.

INDUSTRIAL APPLICABILITY

The liquid phenol resin of the present invention has excellent characteristics of a phenol resin, such as thermal resistance and hardenability, and produces a molded product having excellent flexibility. Therefore, the liquid phenol resin can be suitably used particularly for impregnation.

The invention claimed is:

1. A liquid phenol resin obtained by reacting (A) oils and (B) phenol with (C) a secondary and/or a tertiary alkylamine compound, wherein
a molar ration of (C)/{(A)+(B)} is within a range of 0.13 to 0.35,
the (A) oils include at least one or more kinds selected from the group consisting of cashew oil and tung oil, and
the (C) secondary and/or tertiary alkylamine compound includes hexamethylenetetramine.

2. The liquid phenol resin according to claim 1, wherein a nitrogen content based on the whole liquid phenol resin is 3% by weight to 30% by weight.

3. The liquid phenol resin according to claims 1, wherein a weight ratio between the (A) oils and the (B) phenol is (A):(B)=10:90 to 90:10.

4. The liquid phenol resin according to claim 1, which is used for impregnation.

5. A method of preparing a liquid phenol resin which is the liquid phenol resin according to claim 1, comprising reacting (A) oils and (B) phenol with (C) a secondary and/or a tertiary alkylamine compound without performing a step of dehydration, wherein
a molar ration of (C)/{(A)+(B)} is within a range of 0.13 to 0.35,
the (A) oils include at least one or more kinds selected from the group consisting of cashew oil and tung oil, and
the (C) secondary and/or tertiary alkylamine compound includes hexamethylenetetramine.

* * * * *